United States Patent [19]

Klepel

[11] Patent Number: 5,032,948
[45] Date of Patent: Jul. 16, 1991

[54] DIE CUT DISPOSABLE GROUNDING WRIST STRAP

[75] Inventor: Donald E. Klepel, Oakdale, Minn.

[73] Assignee: Minnesota Mining and Manufacturing Company, St. Paul, Minn.

[21] Appl. No.: 417,836

[22] Filed: Oct. 6, 1989

[51] Int. Cl.⁵ .............................................. H05F 3/02
[52] U.S. Cl. ...................................... 361/220; 439/37
[58] Field of Search ...................... 361/220, 212, 219; 174/55 G, 6; 128/381, 384, 908; 439/37

[56] References Cited

U.S. PATENT DOCUMENTS 3,857,397 12/1974 Brosseau .............................. 128/384
4,698,724 10/1987 Burvee ................................. 361/220

Primary Examiner—J. R. Scott
Assistant Examiner—Brian Johanssen
Attorney, Agent, or Firm—Gary L. Griswold; Walter N. Kirn; Jack V. Musgrove

[57] ABSTRACT

An inexpensive grounding wrist strap and tether for draining excess electrostatic charge, which may be used once and then disposed. The strap and tether are formed integrally and include a conductive strip having a discrete resistance portion for safety considerations. The discrete resistance portion is formed by making a zig-zag pattern of cuts in the conductive strip, thereby increasing the length of the current path through the discrete resistance portion. Due to the slight resistivity of the conductive strip, the lengthened current path results in a discrete resistance being built into the strip. The cuts may be made in the strip at the same time the strip is fashioned out of a sheet of the conductive material, such as carbon loaded polyethylene.

18 Claims, 2 Drawing Sheets

DIE CUT DISPOSABLE GROUNDING WRIST STRAP

BACKGROUND OF THE INVENTION

1. Field of the Invention

The present invention generally relates to devices for preventing sudden electrostatic discharge, and more particularly to a wrist strap having an integral grounding tether, the grounding tether having a resistive portion formed from a conductive polymeric material.

2. Description of the Prior Art

Electrostatic discharge, as well as the mere presence of a static electric field, can be extremely detrimental to sensitive electronic parts. This is particularly true of modern semiconductors and integrated circuits which may be degraded or destroyed by sudden electrical discharge or the presence of a static field in the workplace. Especially sensitive components can be severely affected by an electrical potential as small as 50 volts, yet the simple act of walking has been known to triboelectrically generate a potential of 30,000 volts or more.

The most common tool heretofore used in the battle against electrostatic discharge is a conductive tether which is designed to drain away excess electrostatic buildup. Such tethers are widely used with straps for attachment to the ankle, wrist and body garments. The primary disadvantage of these prior art straps is their relatively high expense. These devices are also bulky and difficult to store, as compared to the subject device. The present invention obviates these problems by providing a disposable wrist strap which is integrally formed with a grounding tether, greatly reducing manufacturing cost. While there are numerous variations of wrist straps and grounding tethers, the inventor is aware of only two patents which disclose an article similar to the present invention, viz., a wrist strap integrally formed with the grounding tether. Those references are U.S. Pat. Nos. 3,857,397 issued to A. Brosseau on Dec. 31, 1974, and 4,698,724 issued to R. Burvee on Oct. 6, 1987.

One danger in the use of grounding tethers is the possibility that the tether may accidentally come into contact with a high voltage source, or may inadvertently be connected to such a source rather than to earth ground. Practitioners in this area have realized that this hazard may be minimized by providing a resistor in series with the tether, usually on the order of one megohm. In this manner, the resistor limits the current flowing through the tether, sparing the user from a high voltage shock. It has, however, been difficult in the past to provide this feature without adding considerable expense to a disposable strap-tether system.

In the Burvee patent (FIG. 9), a discrete resistance is created in the conductive plastic of the tether by forming an extended area of decreased cross-section. This particular version of the Burvee invention is embodied in a product sold by Minnesota Mining and Manufacturing Co. ("3M"--assignee of the present invention) as the Model 2209 disposable grounding wrist strap. The area of decreased cross-section is constructed by heating a portion of the plastic and embossing it, which does not always result in consistent resistance values in the discrete resistance portion. It would, therefore, be desirable and advantageous to devise a grounding wrist strap having a discrete portion of predictable resistance value, the discrete resistance portion being formed in a single step.

Accordingly, the primary object of the present invention is to provide a grounding wrist strap.

Another object of the invention is to provide such a wrist strap which is formed integrally with a grounding tether, thereby reducing expense.

Still another object of the invention is to provide wrist strap and tether having a discrete resistance portion.

Yet another object of the invention is to provide a simplified method of creating such a wrist strap and tether.

SUMMARY OF THE INVENTION

The foregoing objects are achieved in a wrist strap and integral tether comprising a strip of conductive material, a portion of the conductive material having a series of cuts therein which, for purposes of electrical flow, increases the length of that portion of the strip. Due to the volume resistance of the strip, the effective increase in length results in a predictable discrete resistance built into that portion of the strip. The series of cuts may form a pattern which also reduces the cross-section of the current path, amplifying the resistive effect. The conductive strip is preferably insulated except at its distal and proximate ends, the distal end having a contact surface for connection to an electrical ground, and the proximate end having means for securing it to the user's wrist.

BRIEF DESCRIPTION OF THE DRAWINGS

The novel features of the invention are set forth in the appended claims. The invention itself, however, will best be understood by reference to the accompanying drawings, wherein:

DESCRIPTION OF THE PREFERRED EMBODIMENT

Figure 1:
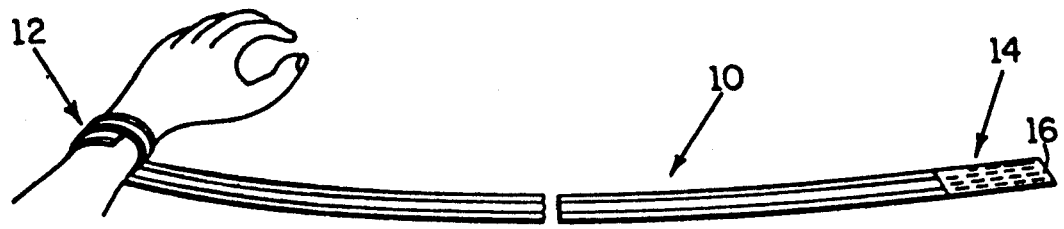
FIG. 1 is a perspective view of the die-cut grounding wrist strap of the present invention with the proximate end thereof being attached to the user's wrist.

With reference now to the figures, and in particular with reference to FIG. 1, there is depicted the die-cut grounding wrist strap 10 of the present invention. The proximate end 12 of wrist strap 10 is designed for direct attachment to a user's wrist (although it could be attached to other areas of the body, e.g., at the ankle, or to body apparel, or to an inanimate object which is to remain grounded). The distal end 14 of wrist strap 10 includes a contact surface 16 for connection to an electrical ground.

Figure 2:
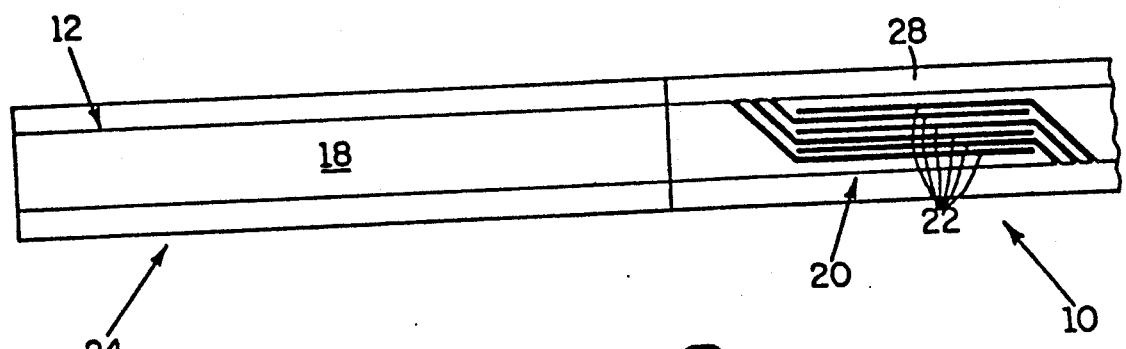
FIG. 2 is a top plan view of the present invention depicting the discrete resistance portion thereof.

With further reference to FIG. 2, the primary element of die-cut wrist strap 10 is a flat strip 18 of conductive material. For reasons that will become apparent, the conductive material must be slightly resistive, preferably having a volume resistivity in the range of 50 to 500 ohms-centimeters. Carbon loaded polyethylene has been found suitable for this purpose, and may be obtained from 3M under the brand name Velostat ("Velostat" is a trademark of 3M). A portion 20 of strip 18 has a plurality of cuts 22 therein which extend essentially through the entire thickness of strip 18. Cuts 22 form a maze-like pattern, with the result that electrical current must flow in a zig-zag manner through portion 20 of strip 18. This effectively increases the length of the current path and, since the conductive material is slightly resistive, forms a discrete resistance in portion 20.

Figure 3:
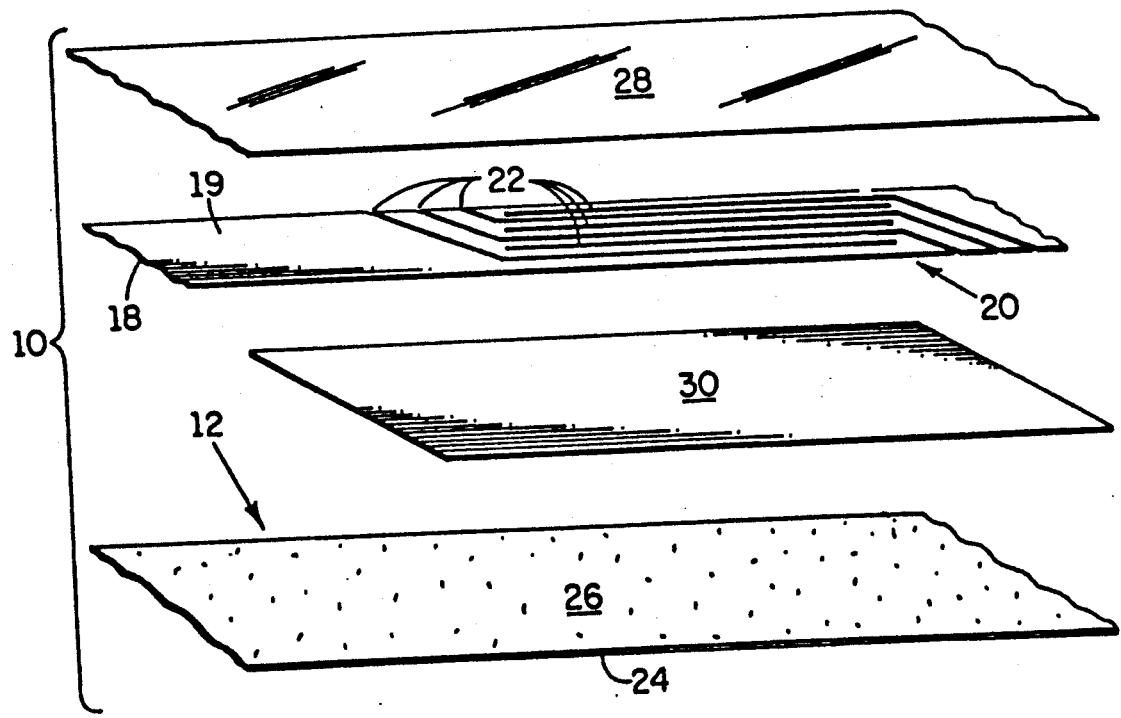
FIG. 3 is an exploded perspective view of the discrete resistance portion of the die-cut grounding wrist strap showing its layered construction.

Referring now to FIG. 3, the layered construction of the preferred embodiment of die-cut wrist strap 10 is illustrated. The lower surface 17 of conductive strip 18 is affixed to a tape 24 having an adhesive layer 26. A suitable tape for this purpose is sold by 3M under the brand name Micropore. Another tape 28 is placed adjacent upper surface 19 of conductive strip 18, and held against tape 24 by adhesive layer 26. Tapes 24 and 28 should both be nonconductive, thereby insulating conductive strip 18 and minimizing the chances of accidental electrical contact between conductive strip 18 and a hazardous electrical potential. Tapes 24 and 28 also impart mechanical integrity to wrist strap 10.

In the preferred embodiment, another layer or small patch 30 is provided. This layer is not necessary in the finished embodiment, but is provided to facilitate the manufacturing process. When the cuts 22 are initially formed in strip 18, the discrete resistance portion 20 is highly susceptible to being pulled apart and damaged. Patch 30 is placed on strip 18 prior to the cutting process and acts as a backing which prevents the unravelling of discrete portion 20. Patch 30 is slightly longer than discrete portion 20, and as wide as layers 24 and 28. Patch 30 is adhered to strip 18 by means of an adhesive coating, and may conveniently be formed from the same material (Micropore tape) as layers 24 and 28.

Tape 28 does not completely extend to proximate end 12 of wrist strap 10. This exposes a portion of conductive strip 18 for direct contact with the skin of the user, and also leaves adhesive layer 26 exposed at proximate end 12. The exposed adhesive assists in the attachment of proximate end 12 to the user's wrist, as shown in FIG. 1. It will also be understood that, while the discrete resistance portion 20 of conductive strip 18 is located near proximate end 12, the die-cut pattern could be placed anywhere along strip 18. It is, however, preferably located near proximate end 12 in order to optimize its usefulness. If conductive strip 18 were exposed to a high-voltage source between ends 12 and 14, the discrete resistance would be ineffective if placed at distal end 24 thereof.

Conductive strip 18 is electrically connected to contact surface 16 at distal end 24 of wrist strap 10. Contact surface 16 may take any convenient form, such as a metallic foil having an electrically conductive adhesive. An example of a copper metal coated with an electrically conductive adhesive is Scotch Brand 1181 tape available from 3M Company ("Scotch" is a trademark of 3M). Other means, such as an alligator clip, are suitable, but a foil strip is less expensive and therefore deemed preferable.

Figure 4A:
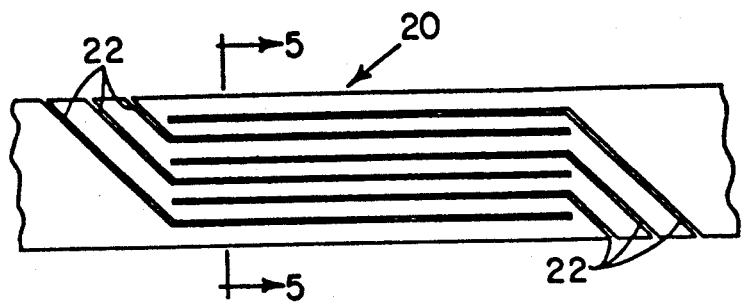
FIGS. 4A through 4D illustrate alternative die-cut patterns.
Figure 4B:
Figure 4C:
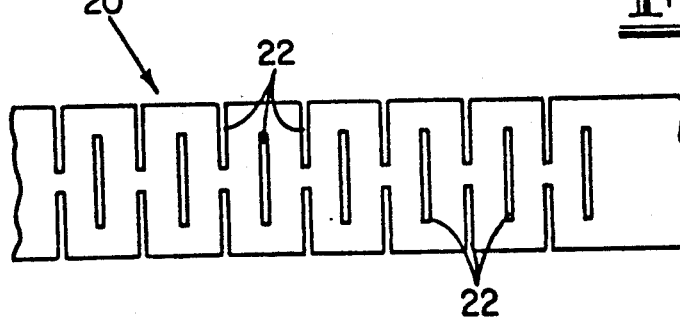
Figure 4D:
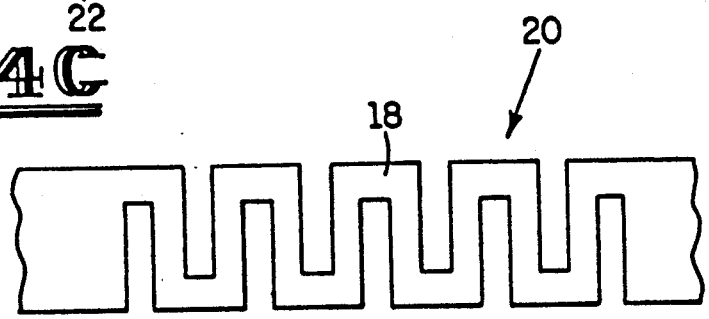
Figure 5:
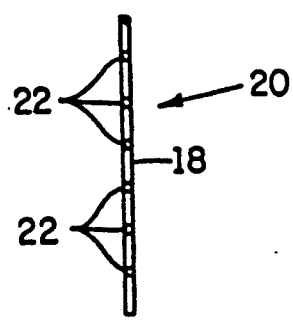
FIG. 5 is a cross-section taken along lines 5—5 of FIG. 4A showing the essentially complete cuts through the conductive polymeric material.

Alternative die-cut patterns are illustrated in FIGS. 4A through 4D. FIG. 4A shows the preferred "seven-path" pattern, while FIGS. 4B and 4C depict zig-zag patterns. In the pattern of FIG. 4D, sections of conductive strip 18 are removed after the die-cutting process (this embodiment is slightly more expense to produce and thus less preferable). The cross-section of FIG. 5 (taken along lines 5—5 of FIG. 4A) highlights the fact that cuts 22 in conductive strip 18 extend essentially through the entire thickness thereof. As those skilled in the art will appreciate, the particular pattern used depends on the thickness of strip 18 and the amount of resistance required, which is usually on the order of one megohm. In order to achieve this value, a Velostat strip having a thickness of between 0.1 millimeters to 0.2 millimeters is preferable (optimally about 0.15 millimeters).

The dimensions of die-cut wrist strap 10 are variable. The length of strap 10 may vary from a couple of feet to several yards, in order to allow connection to distant grounds and still provide freedom of movement at proximate end 12. The width of strap 10 is likewise variable, but in order to minimize the amount of tape 24 used in the fabrication of strap 10 (and hence minimize manufacturing costs), it is preferably no wider than about 3 centimeters, and the width of conductive strip 18 is preferably in the range of 0.5 to 1.5 centimeters (optimally about 0.9 centimeters). Of course, to insure that tape 28 is secured to tape 24, both of these tapes should be wider than strip 18.

The use of a die-cut pattern in the construction of discrete resistance portion 20 results in improved consistency with respect to the value of this resistance, as compared to the prior art. The die-cut pattern also provides additional advantages in the manufacture of wrist strap 10. As noted above, the closest prior art wrist strap (i.e., the Model 2209 wrist strap discussed above in the Description of the Prior Art) requires a two-step heating and embossing process after the conductive material has been cut into a strip. With the present invention, however, the die-cut pattern may be formed simultaneously with the fabrication of conductive strip 18. In other words, the die that is used to cut the conductive material (Velostat) into strips may easily be provided with extra knife rules which form the die-cut pattern. In this regard, the inventor has found that, in order to make clean cuts 22 through conductive strip 18, it is advisable to utilize a heated die.

Use of die-cut grounding wrist strap 10 is straightforward. Prior to handling any static-sensitive components, the user unfolds wrist strap 10 and wraps proximate end 12 around his wrist, the conductive strip 18 contacting the skin. The Contact surface 16 at distal end 14 is attached to an electrical ground. The user is then safely grounded, preventing any electrostatic discharge which might damage electronic components.

Although the invention has been described with reference to specific embodiments, this description is not meant to be construed in a limiting sense. Various modifications of the disclosed embodiment, as well as alternative embodiments of the invention, will become apparent to persons skilled in the art upon reference to the description of the invention. For example, the simplest embodiment might omit tapes 24 and 28 altogether, since these elements are not necessary to provide a path to ground; in such a case, a conductive adhesive may be used to directly affix strip 18 to the user's wrist. It is therefore contemplated that the appended claims will cover such modifications that fall within the true scope of the invention.

I claim:

1. A grounding tether for draining excess electrostatic charge from an object, comprising:

a strip of conductive material having upper and lower surfaces, distal and proximate ends, and having a discrete resistance portion formed by a plurality of cuts which essentially extend through the entire thicknes of said strip said cuts effectively increasing the length of the electrical current path through said discrete resistance portion;

means for attaching said distal end of said strip to an electrical ground; and means for affixing said proximate end of said strip to the object.

2. The grounding tether of claim 1 wherein said attaching means comprises a metallic foil electrically connected to said distal end of said strip, said metallic foil being coated with a conductive adhesive.

3. The grounding tether of claim 1 wherein said strip of conductive material has a volume resistance in the range of 50 to 500 ohms-centimeters.

4. The grounding tether of claim 1 wherein said discrete resistance portion is located near said proximate end of said strip of conductive material.

5. The grounding tether of claim 1 further comprising:

a first insulative tape having a width greater than the width of said strip of conductive material; and a second insulative tape having a width greater than the width of said strip of conductive material, disposed adjacent said upper surface of said strip of conductive material and in partial contact with said adhesive layer of said first insulative tape.

6. The grounding tether of claim 1 wherein said strip of conductive material is formed from a sheet of carbon loaded polyethylene.

7. The grounding tether of claim 1 wherein said plurality of cuts form a zig-zag pattern in said discrete resistance portion of said strip of conductive material.

8. The grounding tether of claim 5 wherein said second insulative tape does not fully extend to said proximate end of said strip of conductive material, thereby exposing a portion of said adhesive layer of said first insulative tape, said exposed portion of said adhesive layer comprising said means for affixing said proximate end to the object.

9. The grounding tether of claim 8 wherein said sheet of carbon loaded polyethylene has a thickness in the range of 0.1 to 0.2 millimeters.

10. The grounding tether of claim 8 wherein said carbon loaded polyethylene has a width in the range of 0.5 to 1.5 centimeters.

11. An integral wrist strap and grounding tether for draining excess electrostatic charge from a user, comprising:

a strip of conductive material having upper and lower surfaces, distal and proximate ends, and having a discrete resistance portion formed by a plurality of cuts which essentially extend through the entire thickness of said strip, said plurality of cuts forming a zig-zag pattern;

a first insulative tape having a width greater than the width of said strip of conductive material, and having an adhesive layer in contact with said lower surface of said strip of conductive material;

a second insulative tape having a width greater than the width of said strip of conductive material, disposed adjacent said upper surface of said strip of conductive material and in partial contact with said adhesive layer of said first insulative tape, said second insulative tape not fully extending to said proximate end of said strip of conductive material, whereby an exposed portion of said adhesive layer may be used to affix said proximate end of said strip to the wrist of the user; and means for attached said distal end of said strip to an electrical ground.

12. The integral wrist strap and grounding tether of claim 11 wherein said attaching means comprises a metallic foil electrically connected to said distal end of said strip, said metallic foil being coated with a conductive adhesive.

13. The integral wrist strap and grounding tether of claim 11 wherein said discrete resistance portion is located near said proximate end of said strip of conduct material.

14. The integral wrist strap and grounding tether of claim 11 wherein said strip of conductive material is formed from a sheet of carbon loaded polyethylene having a volume resistance in the range of 50 to 500 ohms-centimeters.

15. The grounding tether of claim 14 wherein said sheet of carbon loaded polyethylene has a thickness in the range of 0.1 to 0.2 millimeters, and said strip has a width in the range of 0.5 to 1.5 centimeters.

16. A method of manufacturing an integral wrist strap and grounding tether for draining excess electrostatic charge from a user, comprising the steps of:

obtaining a sheet of conductive material having a volume resistivity in the range of 50 to 500 ohms-centimeters; and cutting a strip from said sheet and simultaneously creating a discrete resistance portion in said strip by making a plurality of cuts in said strip, said cuts forming a zig-zag pattern whereby the electrical current path through said discrete resistance portion is effectively lengthened.

17. The method of claim 16 wherein said step of making a plurality of cuts is performed by a heated die.

18. The method of claim 16 further comprising the additional step of placing said strip between two insulative tapes, there being an adhesive layer on at least one of said two tapes, but leaving a portion of said adhesive layer exposed at a proximate end of said strip, said exposed adhesive portion providing means to affix said proximate end to the user's wrist.

* * * * *

UNITED STATES PATENT AND TRADEMARK OFFICE
CERTIFICATE OF CORRECTION

PATENT NO.      :   5,032,948

DATED           :   July 16, 1991

INVENTOR(S)     :   Donald Earl Klepel

It is certified that error appears in the above-identified patent and that said Letters Patent is hereby corrected as shown below:

Column 3, Line 54, "end 24" should read --end 14--.

Column 4, Line 13, change "Vary" to --vary--.

Column 5, Line 25, "material; and" should read --material, and having an adhesive layer in contact with said lower surface of said strip of conductive material;--.

Column 5, Line 44, "claim 8" should read --claim 6--.

Column 5, Line 47, "claim 8" should read --claim 6--.

Column 6, Line 25, "conduct" should read --conductive--.

Signed and Sealed this

Thirtieth Day of March, 1993

*Attest:*

STEPHEN G. KUNIN

*Attesting Officer*    *Acting Commissioner of Patents and Trademarks*